United States Patent
Smith et al.

(10) Patent No.: US 7,532,922 B2
(45) Date of Patent: May 12, 2009

(54) SYSTEM AND METHOD FOR TRANSLATING MEDICAL IMAGING SYSTEM PATIENT TABLES

(75) Inventors: Chad Allan Smith, Milwaukee, WI (US); Kyle Marcus Johnson, Menomonee Falls, WI (US); Timothy Matthew Behlmer, Milwaukee, WI (US); James Loren Dodge, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 868 days.

(21) Appl. No.: 10/915,762

(22) Filed: Aug. 11, 2004

(65) Prior Publication Data

US 2006/0058601 A1 Mar. 16, 2006

(51) Int. Cl.
*A61B 6/04* (2006.01)
*A47B 13/00* (2006.01)
*A61G 7/00* (2006.01)

(52) U.S. Cl. .......................... 600/407; 600/436; 5/601; 5/943

(58) Field of Classification Search ............... 5/601, 5/943, 618, 611; 318/602, 77; 600/427, 600/407, 415; 378/196, 209, 20; 192/48.8, 192/55.1; 601/90; 476/19, 27–34; 366/293–301
See application file for complete search history.

(56) References Cited

U.S. PATENT DOCUMENTS

| | | | |
|---|---|---|---|
| 3,693,381 A * | 9/1972 | McGee ..................... 81/474 |
| 3,825,248 A * | 7/1974 | Friend ..................... 271/10.13 |
| 3,947,902 A * | 4/1976 | Conde et al. .............. 5/81.1 C |
| 3,986,465 A * | 10/1976 | Smith et al. .............. 112/80.32 |
| 4,131,802 A | 12/1978 | Braden et al. |
| 4,225,126 A * | 9/1980 | Lee ........................... 5/613 |
| 4,475,072 A * | 10/1984 | Schwehr et al. ........... 318/602 |
| 4,522,385 A * | 6/1985 | Stefansson ............... 271/10.11 |
| 4,568,071 A * | 2/1986 | Rice ............................ 5/601 |
| 4,609,940 A | 9/1986 | Born et al. |
| 4,651,007 A | 3/1987 | Perusek et al. |
| 4,727,328 A | 2/1988 | Carper et al. |
| 4,771,785 A * | 9/1988 | Duer .......................... 600/415 |
| 4,984,774 A * | 1/1991 | Zupancic et al. ............. 5/601 |
| 5,040,253 A * | 8/1991 | Cheng ......................... 5/616 |
| 5,210,893 A * | 5/1993 | Uosaki et al. ................. 5/601 |
| 5,443,439 A * | 8/1995 | Ohshita ....................... 601/90 |
| 5,804,934 A * | 9/1998 | Yamada et al. ............. 318/77 |
| 6,038,718 A * | 3/2000 | Pennington et al. .......... 5/618 |
| 6,381,780 B1 * | 5/2002 | Nose et al. .................... 5/601 |

(Continued)

*Primary Examiner*—Eric F Winakur
(74) *Attorney, Agent, or Firm*—Dean D. Small; The Small Patent Law Group

(57) ABSTRACT

A system and method for translating a patient table is described. The described patient table includes a linearly translatable portion, a drive screw assembly, a power transmission assembly, and a drive train. The translatable portion is configured to be positioned in a plurality of selectable positions between a fully inserted position and a fully extracted position. The drive screw assembly includes a drive nut and a screw member. The drive nut is fixedly coupled to the translatable portion of the patient table and threadily engaged to the screw member. The screw member is drivingly coupled to the power transmission assembly. The drive train is configured to drive the translatable portion of the patient table at a predetermined insertion force in the insertion direction, and a predetermined extraction force in the extraction direction. The predetermined extraction force is greater than the predetermined insertion force.

24 Claims, 5 Drawing Sheets

U.S. PATENT DOCUMENTS

| | | | |
|---|---|---|---|
| 6,517,232 B1* | 2/2003 | Blue | 366/297 |
| 6,857,147 B2* | 2/2005 | Somasundaram | 5/601 |
| 6,955,464 B1* | 10/2005 | Tybinkowski et al. | 378/209 |
| 7,010,085 B2* | 3/2006 | Kroner et al. | 378/20 |
| 7,065,813 B2* | 6/2006 | Hoth et al. | 5/601 |
| 7,077,569 B1* | 7/2006 | Tybinkowski et al. | 378/209 |
| 7,103,931 B2* | 9/2006 | Somasundaram et al. | 5/601 |
| 2003/0053599 A1* | 3/2003 | Meyer et al. | 378/196 |
| 2003/0212320 A1* | 11/2003 | Wilk et al. | 600/407 |
| 2004/0098804 A1* | 5/2004 | Varadharajulu et al. | 5/611 |
| 2005/0023471 A1* | 2/2005 | Wang et al. | 250/363.04 |
| 2005/0087419 A1* | 4/2005 | Murakami | 192/48.8 |
| 2005/0133330 A1* | 6/2005 | Stiefvater | 192/55.1 |

* cited by examiner

SYSTEM AND METHOD FOR TRANSLATING MEDICAL IMAGING SYSTEM PATIENT TABLES

BACKGROUND OF THE INVENTION

This invention relates generally to medical imaging system patient tables, and more particularly, to drive and control systems in the patient tables.

In medical imaging systems such as PET, a patient is scanned by translating the patient within a bore in a gantry. The gantry includes various detectors that scan the patient. For scanning, the patient is translated along an axis defined by the gantry. A patient table, provided with a drive, supports and translates the patient along the defined axis during the scan. The patient table translates along the defined axis in two directions, namely, an insertion direction and an extraction direction.

In the extraction direction, the patient table drive provides a force to extract the patient from within the gantry. This extraction force needs to be sufficiently large to overcome the forces of friction and loads. In the insertion direction, the patient table drive provides a force to translate the patient within the bore of the gantry. This insertion force needs to be sufficiently small to ensure that the patient or any other person, such as a clinician, may not sustain crushing injuries.

Apart from the above-mentioned requirements, the patient table is required to satisfy some other conditions to ensure the safety of the patient. For example, during any software command, emergency-stop command, or power outage, the patient table needs to be released from the patient table drive, in order to enable drive-free motion, thereby enabling the manual extraction of the patient from within the gantry bore Further, to use the patient table during transportation, such as in a mobile van, the patient table needs to be safely locked for transportation. In conventional patient tables, such as a PET/CT table, a user inserts a transport lock pin, in order to safely lock the patient table for transportation. This may prove hazardous if the user fails to lock the patient table. In addition, the table needs to remain locked if there is a power failure during transportation of the system.

BRIEF DESCRIPTION OF THE INVENTION

In one exemplary embodiment, a method of translating a medical imaging system patient table is provided. The method includes moving a translatable portion of the patient table along a longitudinal axis in extraction and insertion directions. In the extraction direction, the translation is enabled by a drive train that provides an extraction force to the translatable portion. The drive train includes a clutch with a first torque capability in a fully engaged state. This torque is provided when the drive rotates in the extraction direction. In the insertion direction, the translation is enabled through the drive train at a second torque capability, with the clutch slipping at a predetermined torque. The second torque capability is less than the first torque capability.

In another exemplary embodiment, a medical imaging system patient table is provided. The patient table includes a linearly translatable portion, a drive screw assembly, a power transmission assembly, and a drive train. The linearly translatable portion is configured to be positioned in a plurality of selectable positions between a fully inserted and a fully extracted position. The drive screw assembly includes a drive nut and a screw member. The drive nut is fixedly coupled to the translatable portion of the patient table and is threadily engaged to the screw member. The screw member is further drivingly coupled to the power transmission assembly. The drive train is configured to drive the translatable portion of the patient table in the insertion direction at a predetermined insertion force. The drive train is further configured to drive the translatable portion in the extraction direction at a predetermined extraction force. The predetermined extraction force is greater than the predetermined insertion force.

DETAILED DESCRIPTION OF THE INVENTION

Various embodiments of the invention provide methods and systems to control the translation of a medical imaging system patient table. The patient table supports a patient. To enable scanning, such as PET scanning, of various longitudinal portions of the patient, as a part of medical imaging, the patient table is required to translate during scanning. The patient table also needs to be manually extracted from the bore during conditions such as an emergency-stop, power loss or software commands. Emergency-stop commands or software commands may be given by a user when an error is encountered by the medical imaging system, or when conditions occur which may harm the patient or the medical imaging system, or both. The commands may be given through switches or buttons located on the body of the patient table or the medical imaging system.

Figure 1:
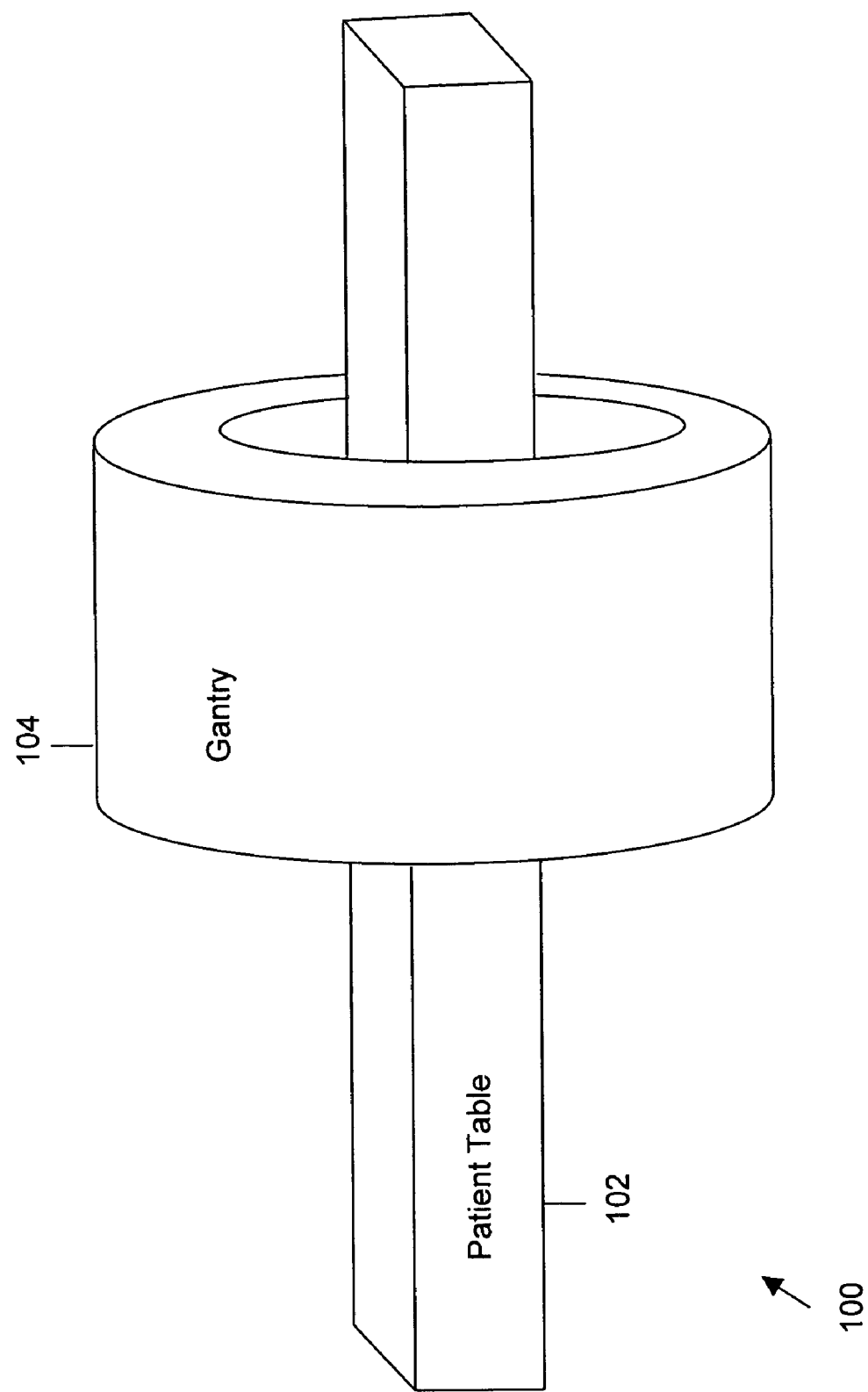
FIG. 1 is a block diagram of a medical imaging system, in accordance with an exemplary embodiment of the invention.

FIG. 1 is a block diagram of a medical imaging system 100, in accordance with various exemplary embodiments of the invention. Medical imaging system 100 includes a patient table 102, as provided by the various embodiments of the invention, and a gantry 104. Patient table 102 translates within a bore in gantry 104. Gantry 104 includes of at least one imaging modality device, such as a detector of medical imaging modality. In accordance with various embodiments of the invention, medical imaging system 100 includes of a Positron Emission Tomography (PET)/Computed Tomography (CT) dual modality scanner. In accordance with various embodiments of the invention, more than one gantry 104 forms a part of medical imaging system 100.

Figure 2:
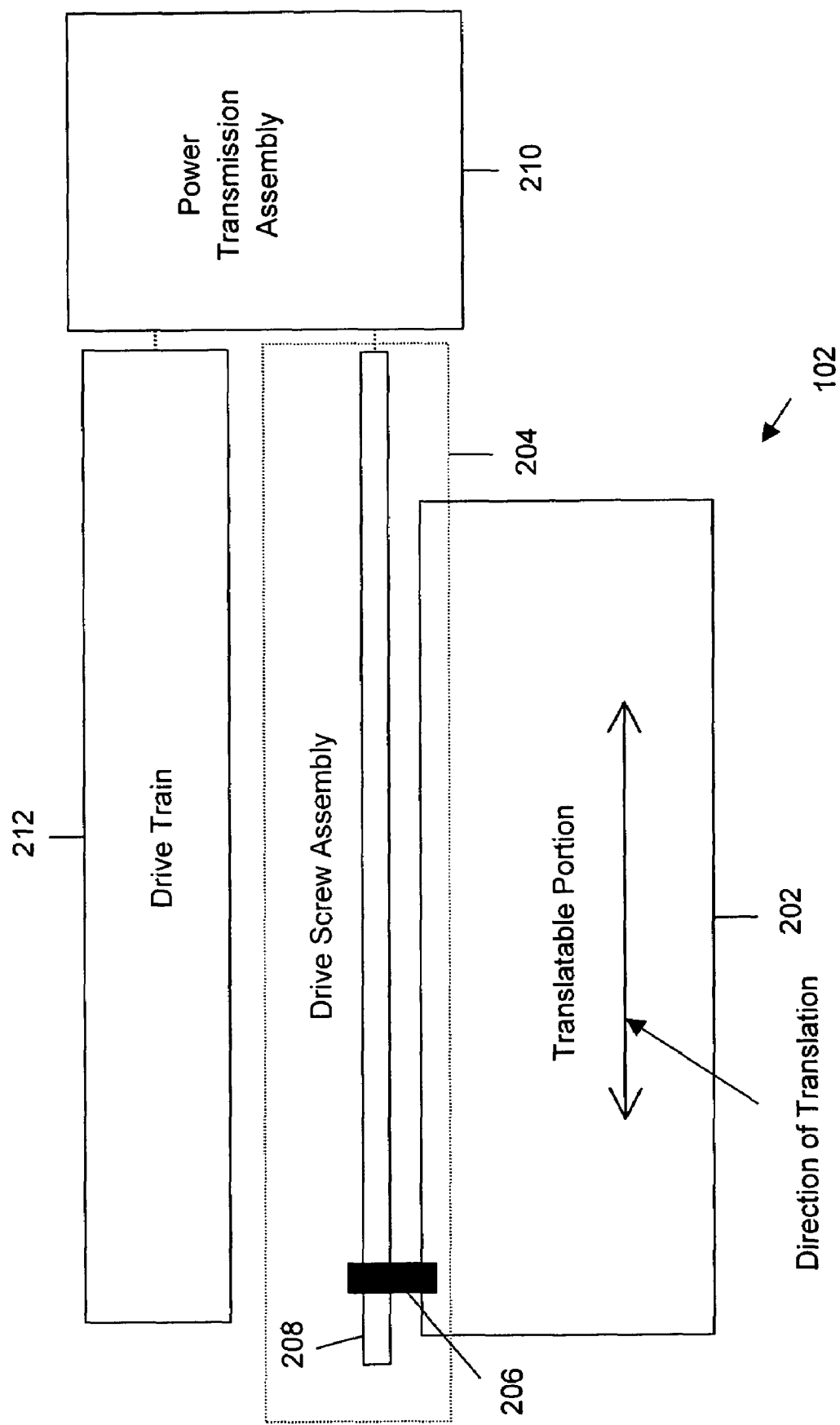
FIG. 2 is a block diagram of a patient table, in accordance with an exemplary embodiment of the invention.

FIG. 2 is a block diagram showing parts of patient table 102, in accordance with various exemplary embodiments of the invention. Patient table 102 includes of a stationary portion, a translatable portion 202, and an assembly involved in driving the translatable portion. The stationary portion of the patient table is not shown in FIG. 2. Translatable portion 202 translates linearly along the direction, as shown in the FIG. 2. One direction of translation, the direction in which patient table 102 is inserted within the bore of gantry 104, is called the insertion direction and the other direction, the direction in which patient table 102 is extracted from within the bore of gantry 104, is called the extraction direction. Translatable portion 202 is configured to translate between two extremes in both the insertion and extraction directions. These two extreme positions are called fully inserted and fully extracted positions, respectively. Translatable portion 202 can also be positioned in a plurality of selectable positions between these two extreme positions.

The assembly involved in driving translatable portion 202 includes a drive screw assembly 204, including a drive nut 206 and a screw member 208, a power transmission assembly 210, and a drive train 212. Translatable portion 202 is coupled to drive screw assembly 204. The coupling is enabled by fixing drive nut 206 to translatable portion 202. Translatable portion 202 is positioned with the help of drive nut 206. Drive nut 206 is engaged to and driven by screw member 208. The rotational motion of screw member 208 is converted to translational motion of drive nut 206, and hence, that of translatable portion 202. In accordance with various embodiments, screw member 208 may be a ball screw or a lead screw.

Screw member 208 is coupled to power transmission assembly 210. In accordance with various embodiments, power transmission assembly 210 includes of a pair of pulleys or sheaves coupled by a belt. In accordance with various other embodiments of the invention, power transmission assembly 210 may include various other power transmitting components, such as, for example, a pair of sprockets coupled by a chain or an assembly of at least two meshed gears.

Power transmission assembly 210 transmits power to screw member 208 from drive train 212. Drive train 212, therefore, drives drive screw assembly 204, and, in turn, translatable portion 202. Drive train 212 is configured to drive translatable portion 202 in both the insertion and extraction directions. The force with which drive train 212 drives translatable portion 202 is predetermined. The driving force in the insertion direction is called the insertion force and that in the extraction direction is called the extraction force. The predetermined value of the extraction force is greater than the predetermined value of the insertion force.

Figure 3:
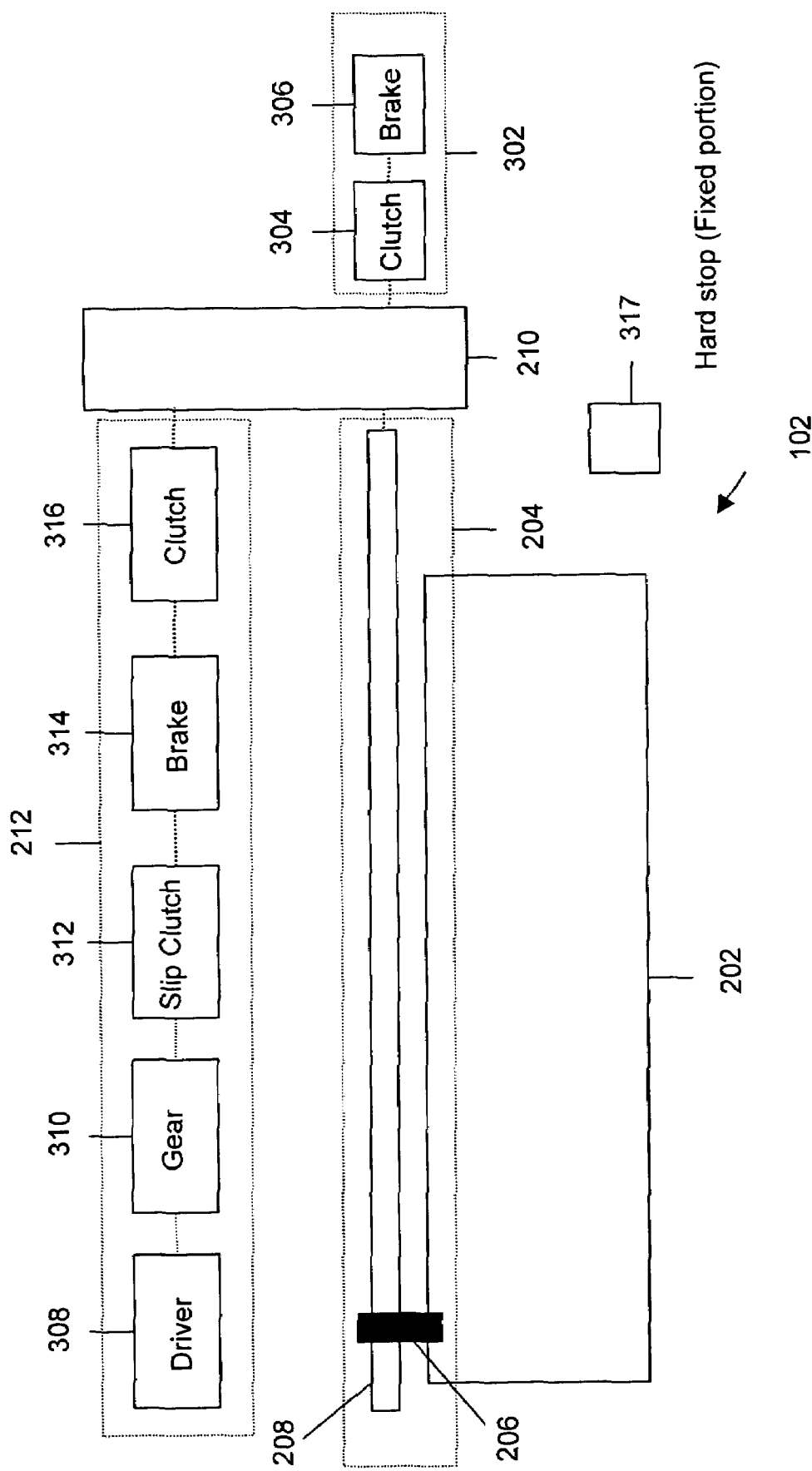
FIG. 3 is a block diagram showing the components of the patient table that control the translation of the translatable portion, in accordance with an exemplary embodiment of the invention.

FIG. 3 is a block diagram showing the components of patient table 102 that control the translation of translatable portion 202, in accordance with various exemplary embodiments of the invention. The translation is controlled by the rotation of drive screw assembly 204.

Patient table 102 further includes a clutch-brake assembly 302, coupled to power transmission assembly 210. Clutch-brake assembly 302 is configured to allow/disallow the rotation of screw member 208. For the purpose of control, clutch-brake assembly 302 includes of a clutch 304 and a brake 306. Brake 306 is coupled to power transmission assembly 210 through clutch 304. In accordance with an embodiment of the invention, brake 306 is engaged when de-energized and released when energized. In the released state of brake 306, clutch-brake assembly 302 permits the rotation of screw member 208 in the insertion as well as the extraction direction. In the brake-engaged state, brake 306 prevents the rotation of screw member 208. However, clutch 304 is configured to rotate freely in the extraction direction and engage in the insertion direction. As a result, clutch 304 permits rotation in extraction direction, while it substantially prevents rotation in insertion direction, when brake 306 is engaged. In accordance with various embodiments of the invention, brake 306 is spring biased in the applied state, i.e., when the brake is de-energized to prevent rotation. In accordance with various embodiments of the invention, clutch 304 is a sprag clutch.

Translation of translatable portion 202 can be further controlled with the help of drive train 212. Drive train 212 may include some or all of the following: a driver 308, a reduction gear 310, a slip clutch 312, a drive train brake 314, and a clutch 316. These components are assembled in a serially operative configuration. The individual components are hereinafter described in detail.

Driver 308 may be a motor that drives the translation of translatable portion 202. Driver 308 is coupled to the components controlling the translation through reduction gear 310. Slip clutch 312 is configured to couple driver 308 to power transmission assembly 210. The coupling enables power transmission in order to rotate screw member 208. Slip clutch 312 fixedly couples its input end to its output end when rotating in the extraction direction. However, when rotating in the insertion direction, it couples its input end to its output end with a selectable torque engagement. In the extraction direction, slip clutch 312 permits only a predetermined first torque, i.e., the extraction torque. However, in the insertion direction, slip clutch 312 is configured to slip at a predetermined second torque. The second torque, which is selectable, is generally lower than the first extraction torque. The second torque can be set by making mechanical adjustments to slip clutch 312. In accordance with various embodiments of the invention, slip clutch 312 is a speciality clutch, i.e., a combination sprag clutch/magnetic hysteresis slip clutch. For example, slip clutch 312 may be a sprag clutch/magnetic hysteresis slip clutch designed by Accu-clutch Company Inc.

Rotation of drive train 212 is prevented when drive train brake 314 is applied, and there is no effect on the rotation when drive train brake 314 is released. In accordance with various embodiments, drive train brake 314 is a power-on brake, i.e., it has no effect when no power is applied and it prevents rotation when power is applied.

Further, clutch 316, within drive train 212, is configured to couple driver 308 to power transmission assembly 210 in a first state, and to disengage driver 308 from power transmission assembly 210 in a second state. In accordance with various embodiments of the invention, clutch 316 engages, i.e., it is in the first state when power is applied, and disengages, i.e., it is in the second state when power is not applied in order to extract a patient in an emergency or power failure. In accordance with various embodiments of the invention, clutch 316 is an electromagnetic clutch.

The control and working of the various components of the patient table, described earlier, is explained in the following description. Patient table 102, as described with reference to FIGS. 1, 2 and 3, enables the performance of functions such as the translation and maintenance of a position of translatable portion 202 of patient table 102. Translation along the extraction direction is driven by the extraction force provided by drive train 212, with slip clutch 312 only permitting the predetermined first torque. Further, the translation along the insertion direction is driven by the insertion force provided by drive train 212, with slip clutch 312 only permitting torque below the predetermined second torque. Slip clutch 312 slips at this predetermined torque, preventing insertion force beyond certain force to drive the translation.

The position of patient table 102 is held under different conditions with the help of drive train brake 314 and clutch-brake assembly 302. Drive train brake 314 holds the position during a medical imaging scan. Drive train brake 314 is therefore generally used in normal working conditions. However, maintaining the position during mobile transport is taken care of by clutch-brake assembly 302 when item 202 is positioned against a rear hard stop (item 317). As described earlier, clutch-brake assembly 302 prevents translation in the insertion direction, and permits translation in the extraction direction. In response to the software command, emergency-stop command, or power outage, clutch 316 disengages translatable portion 202 from drive train 212. As a result, translatable portion 202 can only move with the help of a manual force. Simultaneously, as mentioned earlier, clutch brake assembly 302 prevents the rotation of drive screw assembly 204 in the insertion direction, while allowing rotation in the extraction direction. Consequently, translatable portion 202 can only move in the extraction direction. As translatable portion 202 can translate only within the two extreme positions in the insertion and extraction directions, once fully extracted against hard stop item 317, translatable portion 202 is fully locked.

The manual force, used to manually drive translatable portion 202 in the extraction direction, is needed to pull drive nut 206 for a portion of the length of screw member 208. Screw member 208 rotates in response to this force, applied through drive nut 206. The rotation is at a rate that is proportional to frictional forces between drive nut 206 and screw member 208, and frictional forces internal to power transmission assembly 210.

As described earlier, the translation of patient table 102, as well as holding it at a particular position, is controlled, in accordance with various embodiments of the invention. This control helps to satisfy various safety conditions, in order to ensure the safety of the patient supported on patient table 102, as well as other people, such as clinicians. The safety conditions include automatic locking of patient table 102 at a position, and release of motion during software commands, emergency-stop commands, and power outage. The release of motion allows manual extraction of the patient.

These safety conditions are taken care of by clutch 316, which engages under applied power and releases when applied power is removed. Clutch 316 is positioned between driver 308 and drive screw assembly 204. Clutch 316 disengages during software commands, emergency-stop commands or power outages. This disengaging mechanism releases translatable portion 202 from driver 308. Simultaneously, brake 306 locks the rotation of screw member 208. As a result, patient table 102 is automatically locked.

The release of motion, allowing the manual extraction of the patient, is enabled by clutch 304, which rotates freely in the extraction direction and engages in the insertion direction. As clutch 304 is placed in series between drive screw assembly 204 and brake 306, clutch-brake assembly 302 allows motion in the extraction direction, while preventing the same in the insertion direction. Therefore, clutch-brake assembly 302, along with clutch 316, permits the manual extraction of translatable portion 202, regardless of the state of brake 306.

In summary, during software commands, emergency-stop commands or power outages, clutch 316 releases and brake 306 locks translatable portion 202. The patient can be manually extracted and the patient table is locked in an extracted position until brake 306 is released and clutch 316 engages.

Patient table 102 is also required to prevent an insertion force, higher than a predetermined force, while providing a significant extraction force. Preventing a higher insertion force prevents crushing injury to the patient and clinician. This condition is satisfied by slip clutch 312. Slip clutch 312 provides variable torque adjustment in the insertion direction and a locking torque in the extraction direction. Slip clutch 312 is mechanically adjusted to make adjustments to the predetermined insertion torque. This is needed to calibrate patient table 102 to the insertion force requirement. Slip clutch 312 slips at the adjusted maximum torque in the insertion direction. While rotating in the extraction direction, slip clutch 312 locks the torque to a predetermined torque, which is generally greater than the insertion torque.

Figure 4:
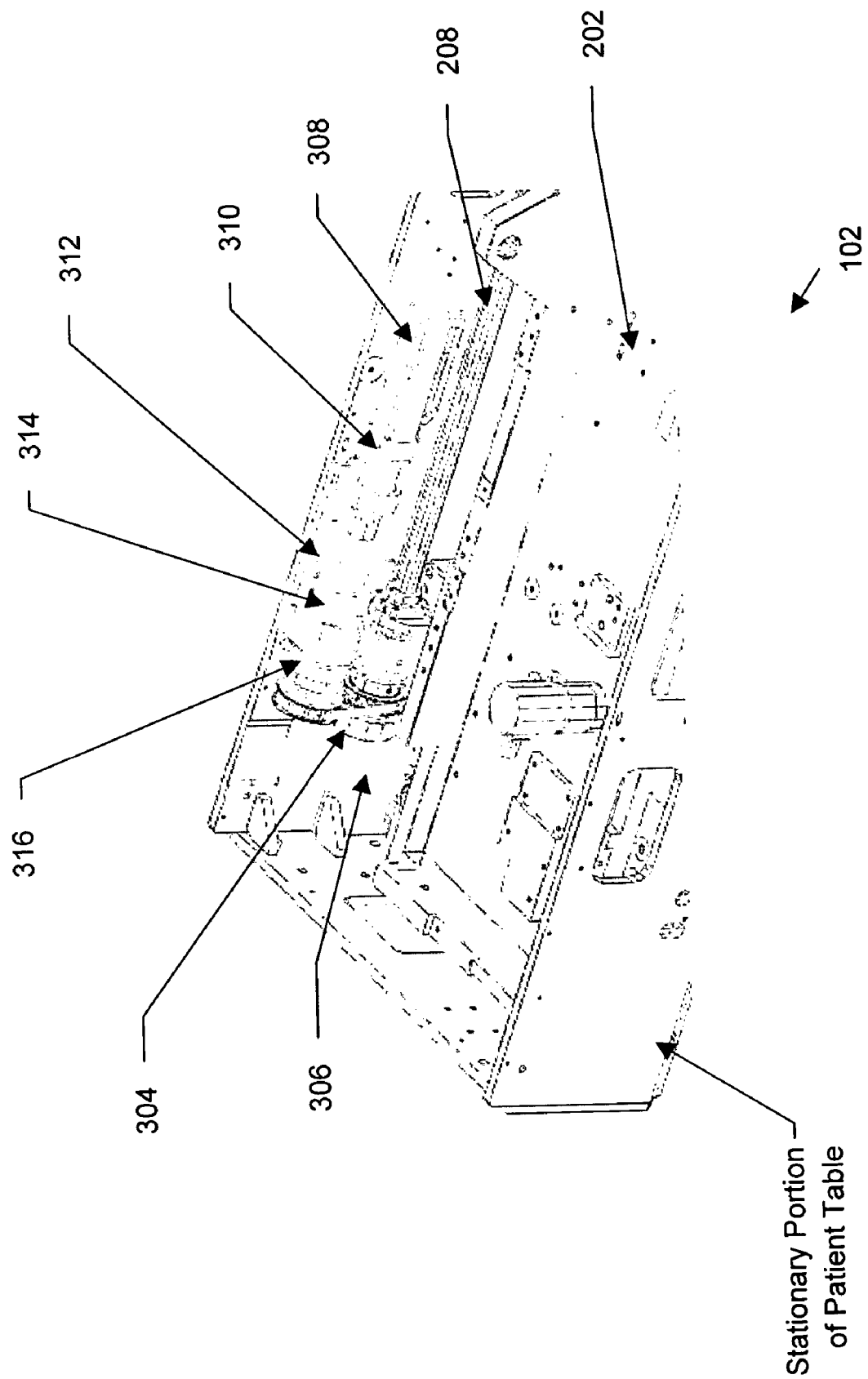
FIG. 4 is a three-dimensional view of the patient table, showing its various components, in accordance with an exemplary embodiment of the invention.

FIG. 4 is a three-dimensional view of patient table 102, showing the various components of the patient table, in accordance with various embodiments of the invention.

Figure 5:
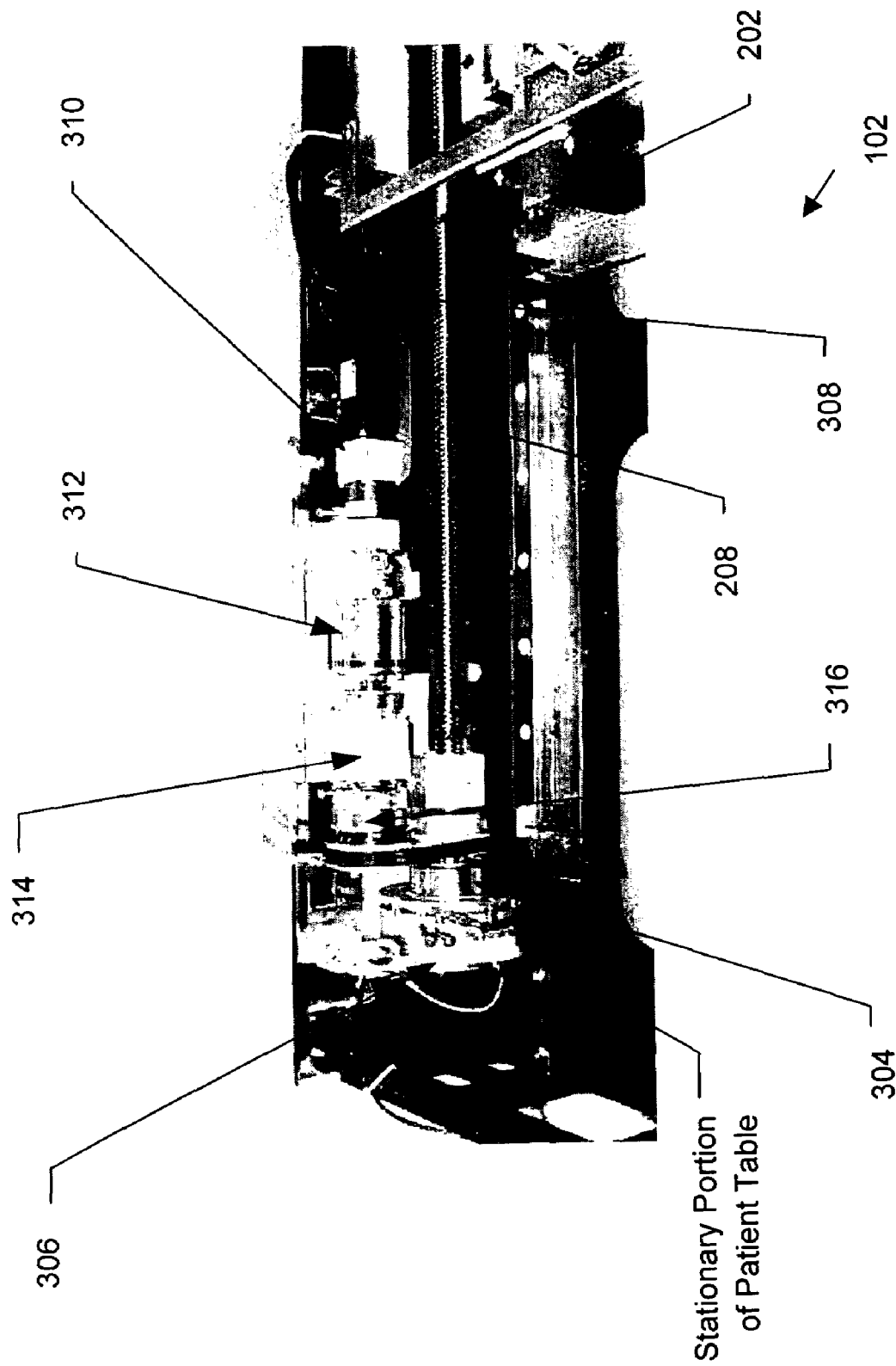
FIG. 5 is an image of a prototype of the patient table, in accordance with an exemplary embodiment of the invention.

FIG. 5 is an image of a prototype of patient table 102, in accordance with various embodiments of the invention.

The various embodiments of the invention satisfy various safety requirements. These safety requirements include automatically locking patient table 102 during a power outage, a software command, or an emergency-stop command. This locking during power outage prevents damage.

Further, the various embodiments of the invention make manual extraction possible during a power outage, a software command, or an emergency-stop command.

Further, the various embodiments of the invention provide a high extraction force and also prevent a large insertion force from driving patient table 102. The large extraction force overcomes friction and loads that may be present. The large insertion force prevents crushing injuries to the patient or clinician.

Further, the various embodiments of the invention provide greater precision movement as a screw, in the form of screw member 208, is used in the driving and positioning mechanism. Therefore, patient table 102 may be useful for performing scans, in case minute adjustments of positions are required. Drive screw assembly 204 also enables patient table 102 to move smoothly between positions, which, in turn, may improve the patient's exam experience.

Further, the various embodiments of the invention provide a lockable drive as a screw, in the form of screw member 208, which is used in the driving mechanism.

Further, the various embodiments of the invention provide patient table 102, which is more compact, allowing the stationary portion of patient table 102 to be shortened. This enables patient table 102 to fit in a standard-sized elevator.

Further, the various embodiments of the invention provide a drive system that is capable of high drive torque.

Further, the various embodiments of the invention provide a system which does not require any manual operations, in order to prepare patient table 102 for transport, such as in a mobile van. Patient table 102 is automatically and safely locked for transport even if a user fails to perform the proper shutdown procedures.

While the invention has been described in terms of various specific embodiments, those skilled in the art will recognize that the invention can be practiced with modification within the spirit and scope of the claims.

What is claimed is:

1. A method of translating a medical imaging system patient table, said method comprising:
    rotating a drive train in a first direction to generate an insertion force;
    transmitting the insertion force through a clutch;
    moving a translatable portion of the patient table along a longiitudinal axis in an insertion extraction direction into a bore of a medical imaging system with the insertion force;
    rotating the drive train in a second direction to generate an extraction force;
    transmitting the extraction force through the clutch;
    moving the translatable portion of the patient table along the longitudinal axis in an extraction direction from the bore with the extraction force;
    wherein, when transmitting the extraction force, the clutch provides a first torque capability in a fully engaged state when rotating in a direction corresponding to the extraction direction and, when transmitting the insertion force, the clutch provides a second torque capability by slipping at a predetermined torque, wherein the second torque capability is less than the first torque capability.

2. A method in accordance with claim 1 further comprising maintaining a position of the translatable portion during a loss of power to the patient table using a clutch-brake assembly wherein the clutch-brake assembly permits manual translation of the translatable portion in the extraction direction and substantially prevents movement of the patient table in the insertion direction.

3. A method in accordance with claim 1 further comprising maintaining a position of the translatable portion during a portion of a medical imaging scan using a drive train brake coupled to a patient table drive screw through a selectably engagable clutch.

4. A method in accordance with claim 1
wherein moving the translatable portion of the patient table along a longitudinal axis in the insertion direction or in the extraction direction comprises rotationally driving a drive screw coupled to the translatable portion with the insertion or extraction force, respectively, through a nut, the insertion and extraction forces transmitted from the drive train through a power transmission assembly to the drive screw.

5. A method of translating a medical imaging system patient table, said method comprising:
moving a translatable portion of the patient table along a longitudinal axis in an extraction direction with a drive train providing an extraction force to the translatable portion, said drive train including a selectably engagable clutch having a first torque capability in a fully engaged state when rotating in a direction corresponding to the extraction direction; and
moving the translatable portion along the longitudinal axis in an insertion direction with the drive train at a second torque capability through the selectably engagable clutch slipping at a predetermined torque wherein the second torque capability is less than the first torque capability; and
manually extracting the patient table from the bore of the medical imaging system during at least one of a loss of power to the patient table and an emergency stop condition wherein the extracting includes disengaging the drive train from the translatable portion using the selectably engagable clutch.

6. A method in accordance with claim 5 wherein manually extracting the patient table comprises using a manual force to pull a drive nut at least a portion of the length of a drive screw, the drive screw rotating in response to the force applied through the drive nut at a rate proportional to a friction force between the drive nut and drive screw and a friction force internal to the power transmission assembly.

7. A medical imaging system patient table comprising:
a linearly translatable portion configured to be positioned in a plurality of selectable positions between a fully inserted position and a fully extracted position;
a drive screw assembly comprising a drive nut fixedly coupled to the translatable portion of the patient table and threadily engaged to a screw member that is drivingly coupled to a power transmission assembly;
a drive train coupled to said power transmission assembly and configured to drive the translatable portion of the patient table in the insertion direction at a predetermined permitted insertion force and to drive the translatable portion in the extraction direction at a predetermined permitted extraction force, said predetermined permitted extraction force being greater than said predetermined permitted insertion force; and
a clutch-brake assembly coupled to the power transmission assembly, said clutch-brake assembly configured to permit rotation of the drive screw in an insertion direction and an extraction direction in a brake released state and substantially prevent rotation in the insertion direction in a brake engaged state.

8. A medical imaging system patient table in accordance with claim 7 wherein said clutch-brake assembly comprises a clutch operatively coupled between said power transmission assembly and a brake.

9. A medical imaging system patient table in accordance with claim 8 wherein said clutch comprises a sprag clutch configured to substantially prevent rotation of the drive screw in the insertion direction when said brake is applied and permits rotation of the drive screw in the extraction direction.

10. A medical imaging system patient table in accordance with claim 8 wherein said brake is configured to be applied when the brake is deenergized and to be released when the brake is energized.

11. A medical imaging system patient table in accordance with claim 10 wherein said brake is spring biased in the applied state when the brake is deenergized.

12. A medical imaging system patient table in accordance with claim 7 wherein said drive screw assembly comprises at least one of a lead screw assembly and a ball screw assembly.

13. A medical imaging system patient table in accordance with claim 7 wherein said power transmission assembly comprises a pair of sheaves coupled by a belt.

14. A medical imaging system patient table in accordance with claim 7 wherein said power transmission assembly comprises a pair of sprockets coupled by a chain.

15. A medical imaging system patient table in accordance with claim 7 wherein said power transmission assembly comprises at least two meshed gears.

16. A medical imaging system patient table in accordance with claim 7 wherein said drive train comprises a clutch configured to couple the drive train to the power transmission assembly in a first state and disengage the drive train from the power transmission assembly in a second state.

17. A medical imaging system patient table in accordance with claim 7 wherein said drive train comprises a slip clutch configured to drivingly couple a driver to the power transmission assembly during rotation in said extraction direction and to slip at a selectable torque during rotation in said insertion direction.

18. A medical imaging system patient table in accordance with claim 7 wherein said drive train comprises a clutch, a drive train brake, and a slip clutch coupled in a serial operative configuration between a driver and the power transmission assembly.

19. A medical imaging system patient table in accordance with claim 18 wherein said clutch is configured to couple the drive train to the power transmission assembly in a first state and disengage the drive train from the power transmission assembly in a second state, said drive train brake is configured to substantially prevent drive train rotation in a first state and to permit drive train rotation in a second state, and said slip clutch is configured to drivingly couple the driver to the power transmission assembly during rotation in said extraction direction and to slip at a selectable torque during rotation in said insertion direction.

20. A medical imaging system patient table comprising:
a linearly translatable portion configured to be positioned in a plurality of selectable positions between a fully inserted position and a fully extracted position;
a drive screw assembly comprising a drive nut fixedly coupled to the translatable portion of the patient table and threadily engaged to a screw member that is drivingly coupled to a power transmission assembly; and a drive train coupled to said power transmission assembly and configured to drive the translatable portion of the patient table in the insertion direction at a predetermined permitted insertion force and to drive the translatable portion in the extraction direction at a predetermined permitted extraction force, said predetermined permitted extraction force being greater than said predetermined permitted insertion force; and wherein said drive train comprises a drive train brake configured to substantially prevent drive train rotation in a first state and to permit drive train rotation in a second state.

21. A medical imaging system comprising:

a gantry comprising a first imaging modality;

a patient table comprising:

a linearly translatable portion configured to be positioned in a plurality of selectable positions between a predetermined fully inserted position and a predetermined fully extracted position;

a drive screw assembly comprising a drive nut fixedly coupled to the translatable portion of the patient table and threadily engaged to a screw member that is drivingly coupled to a power transmission assembly;

a clutch-brake assembly coupled to the power transmission assembly, said clutch-brake assembly configured to permit rotation of the drive screw in an insertion direction and an extraction direction in a brake released state and substantially prevent rotation in the insertion direction in a brake engaged state; and a drive train coupled to said power transmission assembly and configured to drive the translatable portion of the patient table in the insertion direction at a predetermined permitted insertion force and to drive the translatable portion in the extraction direction at a predetermined permitted extraction force, said predetermined permitted extraction force being greater than said predetermined permitted insertion force.

22. A medical imaging system in accordance with claim 21 wherein said gantry comprises a second imaging modality.

23. A medical imaging system in accordance with claim 21 further comprising a second gantry comprising a second imaging modality.

24. A medical imaging system in accordance with claim 21 comprising a positron emission tomography (PET)/computed tomography (CT) dual modality scanner defining the first imaging modality.

* * * * *